United States Patent [19]

Merianos

[11] Patent Number: 5,496,842
[45] Date of Patent: Mar. 5, 1996

[54] SYNERGISTIC WATER SOLUBLE PRESERVATIVE COMPOSITIONS OF BIOCIDAL MIXTURES

[75] Inventor: John J. Merianos, Middletown, N.J.

[73] Assignee: ISP Chemicals Inc., Chatham, N.J.

[21] Appl. No.: 392,635

[22] Filed: Feb. 22, 1995

Related U.S. Application Data

[62] Division of Ser. No. 234,089, Apr. 28, 1994, Pat. No. 5,428,050.
[51] Int. Cl.$^6$ ............................ A01N 43/50; A01N 47/10
[52] U.S. Cl. ........................ 514/389; 514/390; 514/478; 514/479
[58] Field of Search ................... 514/478, 479, 514/389

[56] References Cited

U.S. PATENT DOCUMENTS 4,844,891  7/1989  Rosen et al. ........................ 424/76.4

*Primary Examiner*—Allen J. Robinson
*Attorney, Agent, or Firm*—Walter Katz; Marilyn J. Maue; Joshua J. Ward

[57] ABSTRACT

A water soluble preservative admixture of biocidal compounds for addition to commercial use compositions at predetermined use levels, and uniformly distributed therein, to provide long-time synergistic biocidal activity against a wide range of fungi and both gram-negative and gram-positive bacteria, which comprises powders of (a) one or more methylol compounds, or their equivalents, and (b) iodopropynyl alcohol, or its ester, carbamate or ether derivative thereof, in a weight ratio of (a):(b) of 100:1 to 2000:1.

8 Claims, No Drawings

SYNERGISTIC WATER SOLUBLE PRESERVATIVE COMPOSITIONS OF BIOCIDAL MIXTURES

This is a division of application Ser. No. 08/234,089, filed Apr. 28, 1994, now U.S. Pat. No. 5,428,050 issued Jun. 27, 1993.

BACKGROUND OF THE INVENTION

1. Field of the Invention

This invention relates to a water soluble preservative admixture for addition to commercial use formulations to provide long time synergistic biocidal activity therein, and, more particularly, to admixtures of a methylol compound and an iodopropynyl compound, in predetermined weight ratios of 100:1 to 2000:1.

2. Description of the Prior Art

Combinations of antimicrobial agents have been developed in the prior art in order to:

(1) produce a biochemical synergism;
(2) broaden the antimicrobial spectrum of activity of each agent;
(3) increase water solubility for the admixture;
(4) minimize the toxicity or irritation of a given agent to the host; and
(5) minimize physical and chemical incompatibilities.

True biological synergism exists when two agents, when combined, require lesser amounts of the agents to bring about the same inhibitory or cidal effect than either single agent alone. While synergistic interaction for two or more antimicrobial agents does produce more than merely an additive effect in the resultant biological activity, in most cases the mechanism of such synergism remains a mystery.

M. Rosen et al., in U.S. Pat. No. 4,844,891, for example, described a preservative admixture of (a) a formaldehyde donor and (b) a halopropynyl compound, in a weight ratio of (a):(b) of 50:1 to 1:1, preferably 30:1 to 2:1, and, most preferably, 20:1 to 10:1, as providing fungicidal activity for 1–3 days in commercial use formulations. However, Rosen observed that when the ratio of (a):(b) in the concentrate exceeded 50:1 (System No. 16 in Table 1, a ratio of 73.33), the preservative composition was ineffective in providing biocidal protection in the use formulations. Thus a relatively large amount of the halopropynyl compound was required by Rosen to provide significant biocidal activity in the use composition. In such admixtures, although the formaldehyde donor is water soluble, the halopropynyl compound is substantially insoluble in water. Therefore it was difficult for Rosen to uniformly distribute his admixture throughout the use composition.

For these and other reasons, it is desired to provide a new and improved water soluble preservative admixture of such biocidal compounds which requires relatively little of the water insoluble and expensive halopropynyl compound, and that also provides effective synergistic protection in use formulations against a wide range of fungi and bacteria at different use levels over a long period of time.

A feature of the present invention is the provision of an admixture concentrate which is water soluble and which therefore can be uniformly distributed in use compositions at a predetermined use level.

Another feature herein is the provision of a preservative admixture which exhibits a long term synergistic biocidal activity against wide range of fungi and both gram-negative and gram-positive bacteria in the use compositions.

Still another feature of this invention is the provision of a water soluble preservative admixture for personal care compositions in the form of a solution, lotion, gel, emulsion, emulsifiable concentrate, suspension, slurry or cream.

These and other objects and features of the invention will be made apparent from the following more particular description of the invention.

SUMMARY OF THE INVENTION

What has been discovered is a water soluble preservative composition for addition to commercial use compositions at predetermined use levels, and uniformly distributed therein, which provides long term synergistic biocidal activity against a wide range of fungi and both gram-negative and gram-positive bacteria. The composition of the invention comprises an admixture of powders of (a) a methylol compound, or their equivalent, and
(b) iodopropynyl alcohol, or its ester, carbamate or ether derivative thereof, in a weight ratio of (a):(b) of 100:1 to 2000:1, preferably 200:1 to 500:1.

Commercial use compositions containing about 0.01 to 2% by weight of the composition of the invention also are provided therein. Such use compositions contain an iodopropynyl compound in an amount of about 0.5 to 10 ppm, to provide the desired antifungal activity, and a methylol compound, or equivalent thereof, in an amount of at least 250 ppm, to provide the desired antibacterial activity.

DETAILED DESCRIPTION OF THE INVENTION

The invention is based upon the discoveries that in a predetermined admixture of (a) a methylol compound, or its equivalent, and (b) an iodopropynyl compound:

(1) Iodopropynyl compounds are substantially water insoluble at weight ratios of (a):(b) of less than 100; accordingly at weight ratios below 100:1, it is difficult to uniformly distribute the iodopropynyl compound in aqueous use compositions, particularly in creams, gels and the like. In this invention, the admixtures are used at a weight ratio of (a):(b) of 100:1 to 2000:1, which are water soluble in all use compositions at conventional use levels.

(2) Effective synergistic biocidal activity is achieved for admixtures having a weight ratio of (a):(b) of 100:1 to 2000:1. Such admixtures have a Synergistic Index (SI) value approaching zero (maximum synergism) for a wide range of organisms. In contrast, admixtures with (a):(b) ratios below 100:1, e.g. 10:1 to 50:1, are much less synergistic, and are active with only a narrower range of organisms.

(3) Preservative activity for use compositions is achieved most effectively with an admixture wt. ratio of 100:1 to 2000:1 at use levels of 0.05 to 2% by weight of the finished product. In this amount, the iodopropynyl compound is present in an amount of only 0.5–10 ppm, which significantly reduces the cost and toxicity of the use composition. The methylol compound also is present in an amount of at least 250 ppm.

The experimental results upon which these discoveries are based are described below. In these examples, the (a) methylol compound may be selected from diazolidinyl urea (GERMALL® II) N-[1,3-bis(hydroxymethyl)-2,5-dioxo-4-imidazolidinyl]N,N'-bis(hydroxymethyl) urea imidurea (GERMALL® 115), 1,3-dimethylol-5,5-dimethyl hydantoin (DMDMH), sodium hydroxymethylglycinate (SUT- TOCIDE® A), glycine anhydride dimethylol (GADM), dimethylhydroxymethyl pyrazole, (1-(3-chloroallyl)-3,5,7-triaza-1-azoniaadamantane chloride (a methylol equivalent), 1,3,5-(trishydroxyethyl)hexahydrotriazine, or hydroxymethyl pyrrolidone; and the (b) iodopropynyl compound is iodopropynyl alcohol (IPGA) or 3-iodo-2-propynylbutyl carbamate (IPBC).

1. WATER SOLUBILITY

The water solubility or insolubility of admixtures of several methylol compounds with IPBC as 1% aqueous solutions is shown in Tables A through C below.

TABLE A

| Weight Ratio of Germall® II:IPBC | Amount in ppm | Solubility |
|---|---|---|
| 2000:1 | 5 | Soluble |
| 1000:1 | 10 | Soluble |
| 500:1 | 20 | Soluble |
| 200:1 | 50 | Soluble |
| 100:1 | 100 | Soluble |
| 50:1 | 200 | Insoluble |
| 20:1 | 500 | Insoluble |

TABLE B

| Weight Ratio of GADM:IPBC | Amount in ppm | Solubility |
|---|---|---|
| 2000:1 | 5 | Soluble |
| 1000:1 | 10 | Soluble |
| 500:1 | 20 | Soluble |
| 200:1 | 50 | Soluble |
| 100:1 | 100 | Soluble |
| 50:1 | 200 | Insoluble |
| 20:1 | 500 | Insoluble |

TABLE C

| Weight Ratio of DMDMH:IPBC | Amount in ppm | Solubility |
|---|---|---|
| 2000:1 | 5 | Soluble |
| 1000:1 | 10 | Soluble |
| 500:1 | 20 | Soluble |
| 200:1 | 50 | Soluble |

TABLE C-continued

| Weight Ratio of DMDMH:IPBC | Amount in ppm | Solubility |
|---|---|---|
| 100:1 | 100 | Soluble |
| 50:1 | 200 | Insoluble |
| 20:1 | 500 | Insoluble |

These results demonstrate that admixtures having a ratio of 50:1 or 20:1 are insoluble in water whereas at ratios of 100:1 to 2000:1 the admixtures are soluble in water.

2. SYNERGISM

Tables 1 through 14 below demonstrate the very effective synergistic interaction between compounds "a" and "b" against a broad range of fungi and both gram-negative and gram-positive bacteria. The following organisms were tested:

| Organism | ATCC Number | Inoculum | Concentration |
|---|---|---|---|
| Ps. aeruginosa (PSA)* | 9027 | $2.1 \times 10^6$ | CFU/gm of Product |
| E. coli (ECOLI)* | 8739 | $4.7 \times 10^5$ | CFU/gm of Product |
| Staph. aureus (SA)** | 6538 | $1.6 \times 10^6$ | CFU/gm of Product |
| Ps. cepacia (PC)* | 25416 | $1.6 \times 10^6$ | CFU/gm of Product |
| C. albicans (CAN)*** | 10231 | $8.0 \times 10^4$ | CFU/gm of Product |
| A. niger (AN)*** | 16404 | $2.7 \times 10^5$ | CFU/gm of Product |

*gram-negative bacteria
**gram-positive bacteria
***fungi

Table D below lists the static (MIC) and cidal activities of several antimicrobial agents in ppm. These activities are used to calculate the Synergism Index (SI) of admixtures of the present invention.

TABLE D

Static (MIC) and Cidal Activities of Several Antimicrobial Compounds
(Static/Cidal Concentrations in ppm)

| Organism (ATCC #) | IPBC | Germall® II | GADM | DMDMH | IPGA |
|---|---|---|---|---|---|
| (SA) (6538) | 100/200 | 400/1600 | 400/800 | 450/1600 | 300/5000 |
| (ECOLI) (8739) | 50/100 | 400/1600 | 400/800 | 400/800 | 150/600 |
| (PSA) (9027) | 800/1200 | 400/1600 | 400/400 | 600/1600 | 70/70 |
| (PC) (25416) | 1200/1800 | 200/400 | 200/400 | 600/1600 | 70/300 |
| (CAN) (10231) | 50/100 | 1500/15000 | 7500/15000 | 8000/16000 | 50/300 |
| (AN) (16404) | 50/100 | 3200/3200 | 1600/3200 | 8000/16000 | 30/30 |

The Synergism Index was determined by the same mathematical treatment of such data described by Kull et al. in Applied Microbiology 9, 538–541 (1961) using the following relationship:

$$\text{Synergism Index } (SI) = \frac{Q_A}{Q_a} + \frac{Q_B}{Q_b}$$

where:

1. $Q_a$ = The quantity of Compound a acting alone, producing an endpoint.
2. $Q_b$ = The quantity of Compound b acting alone, producing and endpoint.
3. $Q_A$ = The quantity of Compound $\underline{A}$ in mixture, producing an endpoint.
4. $Q_B$ = The quantity of Compound $\underline{B}$ in mixture, producing an endpoint.

When SI is equal to 1, a mere additive effect of the components in the mixture is indicated; when SI is less than 1, synergism has occurred; and when SI is greater than 1 it indicates antagonism of the two components.

According to this well known method of measuring synergism, the quantity of each component in the various mixtures is compared with the quantity of pure component that is required to reach the same endpoint or to produce the same microbiological effect as the mixture.

TABLE 1

2000:1 Wt. Ratio GERMALL ® II/IPBC

| Use Level | Organism | $Q_a$ | $Q_b$ | $Q_A$ | $Q_B$ | SI |
|---|---|---|---|---|---|---|
| 0.01% | SA | 200 | 1600 | 0.05 | 99.95 | 0.06 |
| " | ECOLI | 100 | 1600 | 0.05 | 99.95 | 0.06 |
| " | PSA | 1200 | 1600 | 0.05 | 99.95 | 0.06 |
| " | PC | 1800 | 1250 | 0.05 | 99.95 | 0.08 |
| " | CAN | 100 | 15000 | 0.05 | 99.95 | 0.01 |
| " | AN | 100 | 3200 | 0.05 | 99.95 | 0.03 |
| 0.025% | SA | 200 | 1600 | 0.125 | 249.9 | 0.16 |
| " | ECOLI | 100 | 1600 | 0.125 | 249.9 | 0.16 |
| " | PSA | 1200 | 1600 | 0.125 | 249.9 | 0.16 |
| " | PC | 1800 | 1250 | 0.125 | 249.9 | 0.20 |
| " | CAN | 100 | 15000 | 0.125 | 249.9 | 0.02 |
| " | AN | 100 | 3200 | 0.125 | 249.9 | 0.08 |
| 0.05% | SA | 200 | 1600 | 0.25 | 499.8 | 0.31 |
| " | ECOLI | 100 | 1600 | 0.25 | 499.8 | 0.31 |
| " | PSA | 1200 | 1600 | 0.25 | 499.8 | 0.31 |
| " | PC | 1800 | 1250 | 0.25 | 499.8 | 0.40 |
| " | CAN | 100 | 15000 | 0.25 | 499.8 | 0.04 |
| " | AN | 100 | 3200 | 0.25 | 499.8 | 0.16 |
| 0.10% | SA | 200 | 1600 | 0.5 | 999.5 | 0.63 |
| " | ECOLI | 100 | 1600 | 0.5 | 999.5 | 0.63 |
| " | PSA | 1200 | 1600 | 0.5 | 999.5 | 0.63 |
| " | PC | 1800 | 1250 | 0.5 | 999.5 | 0.80 |
| " | CAN | 100 | 15000 | 0.5 | 999.5 | 0.07 |
| " | AN | 100 | 3200 | 0.5 | 999.5 | 0.32 |
| 0.20% | SA | 200 | 1600 | 1 | 1999 | 1.25 |
| " | ECOLI | 100 | 1600 | 1 | 1999 | 1.26 |
| " | PSA | 1200 | 1600 | 1 | 1999 | 1.25 |
| " | PC | 1800 | 1250 | 1 | 1999 | 1.60 |
| " | CAN | 100 | 15000 | 1 | 1999 | 0.14 |
| " | AN | 100 | 3200 | 1 | 1999 | 0.63 |
| 0.40% | SA | 200 | 1600 | 2 | 3998 | 2.51 |
| " | ECOLI | 100 | 1600 | 2 | 3998 | 2.52 |
| " | PSA | 1200 | 1600 | 2 | 3998 | 2.50 |
| " | PC | 1800 | 1250 | 2 | 3998 | 3.20 |
| " | CAN | 100 | 15000 | 2 | 3998 | 0.29 |
| " | AN | 100 | 3200 | 2 | 3998 | 1.27 |
| 0.50% | SA | 200 | 1600 | 2.5 | 4997.5 | 3.14 |
| " | ECOLI | 100 | 1600 | 2.5 | 4997.5 | 3.15 |
| " | PSA | 1200 | 1600 | 2.5 | 4997.5 | 3.13 |
| " | PC | 1800 | 1250 | 2.5 | 4997.5 | 4.00 |
| " | CAN | 100 | 15000 | 2.5 | 4997.5 | 0.36 |
| " | AN | 100 | 3200 | 2.5 | 4997.5 | 1.59 |

TABLE 2

1000:1 Wt. Ratio GERMALL ® II/IPBC

| Use Level | Organism | $Q_a$ | $Q_b$ | $Q_A$ | $Q_B$ | SI |
|---|---|---|---|---|---|---|
| 0.01% | SA | 200 | 1600 | 0.1 | 99.9 | 0.06 |
| " | ECOLI | 100 | 1600 | 0.1 | 99.9 | 0.06 |
| " | PSA | 1200 | 1600 | 0.1 | 99.9 | 0.06 |
| " | PC | 1800 | 1250 | 0.1 | 99.9 | 0.08 |
| " | CAN | 100 | 15000 | 0.1 | 99.9 | 0.01 |
| " | AN | 100 | 3200 | 0.1 | 99.9 | 0.03 |
| 0.025% | SA | 200 | 1600 | 0.25 | 249.8 | 0.16 |
| " | ECOLI | 100 | 1600 | 0.25 | 249.8 | 0.16 |
| " | PSA | 1200 | 1600 | 0.25 | 249.8 | 0.16 |
| " | PC | 1800 | 1250 | 0.25 | 249.8 | 0.20 |
| " | CAN | 100 | 15000 | 0.25 | 249.8 | 0.02 |
| " | AN | 100 | 3200 | 0.25 | 249.8 | 0.08 |
| 0.05% | SA | 200 | 1600 | 0.5 | 499.5 | 0.31 |
| " | ECOLI | 100 | 1600 | 0.5 | 499.5 | 0.32 |
| " | PSA | 1200 | 1600 | 0.5 | 499.5 | 0.31 |
| " | PC | 1800 | 1250 | 0.5 | 499.5 | 0.40 |
| " | CAN | 100 | 15000 | 0.5 | 499.5 | 0.04 |
| " | AN | 100 | 3200 | 0.5 | 499.5 | 0.16 |
| 0.10% | SA | 200 | 1600 | 1 | 999 | 0.63 |
| " | ECOLI | 100 | 1600 | 1 | 999 | 0.63 |
| " | PSA | 1200 | 1600 | 1 | 999 | 0.63 |
| " | PC | 1800 | 1250 | 1 | 999 | 0.80 |
| " | CAN | 100 | 15000 | 1 | 999 | 0.08 |
| " | AN | 100 | 3200 | 1 | 999 | 0.32 |
| 0.20% | SA | 200 | 1600 | 2 | 1998 | 1.26 |
| " | ECOLI | 100 | 1600 | 2 | 1998 | 1.27 |
| " | PSA | 1200 | 1600 | 2 | 1998 | 1.25 |
| " | PC | 1800 | 1250 | 2 | 1998 | 1.60 |
| " | CAN | 100 | 15000 | 2 | 1998 | 0.15 |
| " | AN | 100 | 3200 | 2 | 1998 | 0.64 |
| 0.40% | SA | 200 | 1600 | 4 | 3996 | 2.52 |
| " | ECOLI | 100 | 1600 | 4 | 3996 | 2.54 |
| " | PSA | 1200 | 1600 | 4 | 3996 | 2.50 |
| " | PC | 1800 | 1250 | 4 | 3996 | 3.20 |
| " | CAN | 100 | 15000 | 4 | 3996 | 0.31 |
| " | AN | 100 | 3200 | 4 | 3996 | 1.29 |
| 0.50% | SA | 200 | 1600 | 5 | 4995 | 3.15 |
| " | ECOLI | 100 | 1600 | 5 | 4995 | 3.17 |
| " | PSA | 1200 | 1600 | 5 | 4995 | 3.13 |
| " | PC | 1800 | 1250 | 5 | 4995 | 4.00 |
| " | CAN | 100 | 15000 | 5 | 4995 | 0.38 |
| " | AN | 100 | 3200 | 5 | 4995 | 1.61 |

TABLE 3

500:1 Wt. Ratio GERMALL ® II/IPBC

| Use Level | Organism | $Q_a$ | $Q_b$ | $Q_A$ | $Q_B$ | SI |
|---|---|---|---|---|---|---|
| 0.01% | SA | 200 | 1600 | 0.2 | 99.8 | 0.06 |
| " | ECOLI | 100 | 1600 | 0.2 | 99.8 | 0.06 |
| " | PSA | 1200 | 1600 | 0.2 | 99.8 | 0.06 |
| " | PC | 1800 | 1250 | 0.2 | 99.8 | 0.08 |
| " | CAN | 100 | 15000 | 0.2 | 99.8 | 0.01 |
| " | AN | 100 | 3200 | 0.2 | 99.8 | 0.03 |
| 0.025% | SA | 200 | 1600 | 0.5 | 249.5 | 0.16 |
| " | ECOLI | 100 | 1600 | 0.5 | 249.5 | 0.16 |
| " | PSA | 1200 | 1600 | 0.5 | 249.5 | 0.16 |
| " | PC | 1800 | 1250 | 0.5 | 249.5 | 0.20 |
| " | CAN | 100 | 15000 | 0.5 | 249.5 | 0.02 |
| " | AN | 100 | 3200 | 0.5 | 249.5 | 0.08 |
| 0.05% | SA | 200 | 1600 | 1 | 499 | 0.32 |
| " | ECOLI | 100 | 1600 | 1 | 499 | 0.32 |
| " | PSA | 1200 | 1600 | 1 | 499 | 0.31 |
| " | PC | 1800 | 1250 | 1 | 499 | 0.40 |
| " | CAN | 100 | 15000 | 1 | 499 | 0.04 |
| " | AN | 100 | 3200 | 1 | 499 | 0.17 |
| 0.10% | SA | 200 | 1600 | 2 | 998 | 0.63 |
| " | ECOLI | 100 | 1600 | 2 | 998 | 0.64 |
| " | PSA | 1200 | 1600 | 2 | 998 | 0.63 |
| " | PC | 1800 | 1250 | 2 | 998 | 0.80 |
| " | CAN | 100 | 15000 | 2 | 998 | 0.09 |
| " | AN | 100 | 3200 | 2 | 998 | 0.33 |

TABLE 3-continued

500:1 Wt. Ratio GERMALL ® II/IPBC

| Use Level | Organism | $Q_a$ | $Q_b$ | $Q_A$ | $Q_B$ | SI |
|---|---|---|---|---|---|---|
| 0.20% | SA | 200 | 1600 | 4 | 1996 | 1.27 |
| " | ECOLI | 100 | 1600 | 4 | 1996 | 1.29 |
| " | PSA | 1200 | 1600 | 4 | 1996 | 1.25 |
| " | PC | 1800 | 1250 | 4 | 1996 | 1.60 |
| " | CAN | 100 | 15000 | 4 | 1996 | 0.17 |
| " | AN | 100 | 3200 | 4 | 1996 | 0.66 |
| 0.40% | SA | 200 | 1600 | 8 | 3992 | 2.54 |
| " | ECOLI | 100 | 1600 | 8 | 3992 | 2.58 |
| " | PSA | 1200 | 1600 | 8 | 3992 | 2.50 |
| " | PC | 1800 | 1250 | 8 | 3992 | 3.20 |
| " | CAN | 100 | 15000 | 8 | 3992 | 0.35 |
| " | AN | 100 | 3200 | 8 | 3992 | 1.33 |
| 0.50% | SA | 200 | 1600 | 10 | 4990 | 3.17 |
| " | ECOLI | 100 | 1600 | 10 | 4990 | 3.22 |
| " | PSA | 1200 | 1600 | 10 | 4990 | 3.13 |
| " | PC | 1800 | 1250 | 10 | 4990 | 4.00 |
| " | CAN | 100 | 15000 | 10 | 4990 | 0.43 |
| " | AN | 100 | 3200 | 10 | 4990 | 1.66 |

TABLE 4

200:1 Wt. Ratio GERMALL ® II/IPBC

| Use Level | Organism | $Q_a$ | $Q_b$ | $Q_A$ | $Q_B$ | SI |
|---|---|---|---|---|---|---|
| 0.01% | SA | 200 | 1600 | 0.5 | 99.5 | 0.06 |
| " | ECOLI | 100 | 1600 | 0.5 | 99.5 | 0.07 |
| " | PSA | 1200 | 1600 | 0.5 | 99.5 | 0.06 |
| " | PC | 1800 | 1250 | 0.5 | 99.5 | 0.08 |
| " | CAN | 100 | 15000 | 0.5 | 99.5 | 0.01 |
| " | AN | 100 | 3200 | 0.5 | 99.5 | 0.04 |
| 0.025% | SA | 200 | 1600 | 1.25 | 248.75 | 0.16 |
| " | ECOLI | 100 | 1600 | 1.25 | 248.75 | 0.17 |
| " | PSA | 1200 | 1600 | 1.25 | 248.75 | 0.16 |
| " | PC | 1800 | 1250 | 1.25 | 248.75 | 0.20 |
| " | CAN | 100 | 15000 | 1.25 | 248.75 | 0.03 |
| " | AN | 100 | 3200 | 1.25 | 248.75 | 0.09 |
| 0.05% | SA | 200 | 1600 | 2.5 | 497.5 | 0.32 |
| " | ECOLI | 100 | 1600 | 2.5 | 497.5 | 0.34 |
| " | PSA | 1200 | 1600 | 2.5 | 497.5 | 0.31 |
| " | PC | 1800 | 1250 | 2.5 | 497.5 | 0.40 |
| " | CAN | 100 | 15000 | 2.5 | 497.5 | 0.06 |
| " | AN | 100 | 3200 | 2.5 | 497.5 | 0.18 |
| 0.10% | SA | 200 | 1600 | 5 | 995 | 0.65 |
| " | ECOLI | 100 | 1600 | 5 | 995 | 0.67 |
| " | PSA | 1200 | 1600 | 5 | 995 | 0.63 |
| " | PC | 1800 | 1250 | 5 | 995 | 0.80 |
| " | CAN | 100 | 15000 | 5 | 995 | 0.12 |
| " | AN | 100 | 3200 | 5 | 995 | 0.36 |
| 0.20% | SA | 200 | 1600 | 10 | 1990 | 1.29 |
| " | ECOLI | 100 | 1600 | 10 | 1990 | 1.34 |
| " | PSA | 1200 | 1600 | 10 | 1990 | 1.25 |
| " | PC | 1800 | 1250 | 10 | 1990 | 1.60 |
| " | CAN | 100 | 15000 | 10 | 1990 | 0.23 |
| " | AN | 100 | 3200 | 10 | 1990 | 0.72 |
| 0.40% | SA | 200 | 1600 | 20 | 3980 | 2.59 |
| " | ECOLI | 100 | 1600 | 20 | 3980 | 2.69 |
| " | PSA | 1200 | 1600 | 20 | 3980 | 2.50 |
| " | PC | 1800 | 1250 | 20 | 3980 | 3.20 |
| " | CAN | 100 | 15000 | 20 | 3980 | 0.47 |
| " | AN | 100 | 3200 | 20 | 3980 | 1.44 |
| 0.50% | SA | 200 | 1600 | 25 | 4975 | 3.23 |
| " | ECOLI | 100 | 1600 | 25 | 4975 | 3.36 |
| " | PSA | 1200 | 1600 | 25 | 4975 | 3.13 |
| " | PC | 1800 | 1250 | 25 | 4975 | 3.99 |
| " | CAN | 100 | 15000 | 25 | 4975 | 0.58 |
| " | AN | 100 | 3200 | 25 | 4975 | 1.80 |

TABLE 5

100:1 Wt. Ratio GERMALL ® II/IPBC

| Use Level | Organism | $Q_a$ | $Q_b$ | $Q_A$ | $Q_B$ | SI |
|---|---|---|---|---|---|---|
| 0.01% | SA | 200 | 1600 | 1 | 99 | 0.07 |
| " | ECOLI | 100 | 1600 | 1 | 99 | 0.07 |
| " | PSA | 1200 | 1600 | 1 | 99 | 0.06 |
| " | PC | 1800 | 1250 | 1 | 99 | 0.08 |
| " | CAN | 100 | 15000 | 1 | 99 | 0.02 |
| " | AN | 100 | 3200 | 1 | 99 | 0.04 |
| 0.025% | SA | 200 | 1600 | 2.5 | 248 | 0.17 |
| " | ECOLI | 100 | 1600 | 2.5 | 248 | 0.18 |
| " | PSA | 1200 | 1600 | 2.5 | 248 | 0.16 |
| " | PC | 1800 | 1250 | 2.5 | 248 | 0.20 |
| " | CAN | 100 | 15000 | 2.5 | 248 | 0.04 |
| " | AN | 100 | 3200 | 2.5 | 248 | 0.10 |
| 0.05% | SA | 200 | 1600 | 5 | 495 | 0.33 |
| " | ECOLI | 100 | 1600 | 5 | 495 | 0.36 |
| " | PSA | 1200 | 1600 | 5 | 495 | 0.31 |
| " | PC | 1800 | 1250 | 5 | 495 | 0.40 |
| " | CAN | 100 | 15000 | 5 | 495 | 0.08 |
| " | AN | 100 | 3200 | 5 | 495 | 0.20 |
| 0.10% | SA | 200 | 1600 | 10 | 990 | 0.67 |
| " | ECOLI | 100 | 1600 | 10 | 990 | 0.72 |
| " | PSA | 1200 | 1600 | 10 | 990 | 0.63 |
| " | PC | 1800 | 1250 | 10 | 990 | 0.80 |
| " | CAN | 100 | 15000 | 10 | 990 | 0.17 |
| " | AN | 100 | 3200 | 10 | 990 | 0.41 |
| 0.20% | SA | 200 | 1600 | 20 | 1980 | 1.34 |
| " | ECOLI | 100 | 1600 | 20 | 1980 | 1.44 |
| " | PSA | 1200 | 1600 | 20 | 1980 | 1.25 |
| " | PC | 1800 | 1250 | 20 | 1980 | 1.60 |
| " | CAN | 100 | 15000 | 20 | 1980 | 0.33 |
| " | AN | 100 | 3200 | 20 | 1980 | 0.82 |
| 0.40% | SA | 200 | 1600 | 40 | 3960 | 2.68 |
| " | ECOLI | 100 | 1600 | 40 | 3960 | 2.88 |
| " | PSA | 1200 | 1600 | 40 | 3960 | 2.51 |
| " | PC | 1800 | 1250 | 40 | 3960 | 3.19 |
| " | CAN | 100 | 15000 | 40 | 3960 | 0.66 |
| " | AN | 100 | 3200 | 40 | 3960 | 1.64 |
| 0.50% | SA | 200 | 1600 | 50 | 4950 | 3.34 |
| " | ECOLI | 100 | 1600 | 50 | 4950 | 3.59 |
| " | PSA | 1200 | 1600 | 50 | 4950 | 3.14 |
| " | PC | 1800 | 1250 | 50 | 4950 | 3.99 |
| " | CAN | 100 | 15000 | 50 | 4950 | 0.83 |
| " | AN | 100 | 3200 | 50 | 4950 | 2.05 |

TABLE 6

50:1 Wt. Ratio GERMALL ® II/IPBC

| Use Level | Organism | $Q_a$ | $Q_b$ | $Q_A$ | $Q_B$ | SI |
|---|---|---|---|---|---|---|
| 0.01% | SA | 200 | 1600 | 2 | 98 | 0.07 |
| " | ECOLI | 100 | 1600 | 2 | 98 | 0.08 |
| " | PSA | 1200 | 1600 | 2 | 98 | 0.06 |
| " | PC | 1800 | 1250 | 2 | 98 | 0.08 |
| " | CAN | 100 | 15000 | 2 | 98 | 0.03 |
| " | AN | 100 | 3200 | 2 | 98 | 0.05 |
| 0.025% | SA | 200 | 1600 | 5 | 245 | 0.18 |
| " | ECOLI | 100 | 1600 | 5 | 245 | 0.20 |
| " | PSA | 1200 | 1600 | 5 | 245 | 0.16 |
| " | PC | 1800 | 1250 | 5 | 245 | 0.20 |
| " | CAN | 100 | 15000 | 5 | 245 | 0.07 |
| " | AN | 100 | 3200 | 5 | 245 | 0.13 |
| 0.05% | SA | 200 | 1600 | 10 | 490 | 0.36 |
| " | ECOLI | 100 | 1600 | 10 | 490 | 0.41 |
| " | PSA | 1200 | 1600 | 10 | 490 | 0.31 |
| " | PC | 1800 | 1250 | 10 | 490 | 0.40 |
| " | CAN | 100 | 15000 | 10 | 490 | 0.13 |
| " | AN | 100 | 3200 | 10 | 490 | 0.25 |
| 0.10% | SA | 200 | 1600 | 20 | 980 | 0.71 |
| " | ECOLI | 100 | 1600 | 20 | 980 | 0.81 |
| " | PSA | 1200 | 1600 | 20 | 980 | 0.63 |
| " | PC | 1800 | 1250 | 20 | 980 | 0.80 |
| " | CAN | 100 | 15000 | 20 | 980 | 0.27 |
| " | AN | 100 | 3200 | 20 | 980 | 0.51 |

TABLE 6-continued

50:1 Wt. Ratio GERMALL ® II/IPBC

| Use Level | Organism | $Q_a$ | $Q_b$ | $Q_A$ | $Q_B$ | SI |
|---|---|---|---|---|---|---|
| 0.20% | SA | 200 | 1600 | 40 | 1960 | 1.43 |
| " | ECOLI | 100 | 1600 | 40 | 1960 | 1.63 |
| " | PSA | 1200 | 1600 | 40 | 1960 | 1.26 |
| " | PC | 1800 | 1250 | 40 | 1960 | 1.59 |
| " | CAN | 100 | 15000 | 40 | 1960 | 0.53 |
| " | AN | 100 | 3200 | 40 | 1960 | 1.01 |
| 0.40% | SA | 200 | 1600 | 80 | 3920 | 2.85 |
| " | ECOLI | 100 | 1600 | 80 | 3920 | 3.25 |
| " | PSA | 1200 | 1600 | 80 | 3920 | 2.52 |
| " | PC | 1800 | 1250 | 80 | 3920 | 3.18 |
| " | CAN | 100 | 15000 | 80 | 3920 | 1.06 |
| " | AN | 100 | 3200 | 80 | 3920 | 2.03 |
| 0.50% | SA | 200 | 1600 | 100 | 4900 | 3.56 |
| " | ECOLI | 100 | 1600 | 100 | 4900 | 4.06 |
| " | PSA | 1200 | 1600 | 100 | 4900 | 3.15 |
| " | PC | 1800 | 1250 | 100 | 4990 | 3.98 |
| " | CAN | 100 | 15000 | 100 | 4900 | 1.33 |
| " | AN | 100 | 3200 | 100 | 4900 | 2.53 |

TABLE 7

20:1 Wt. Ratio GERMALL ® II/IPBC

| Use Level | Organism | $Q_a$ | $Q_b$ | $Q_A$ | $Q_B$ | SI |
|---|---|---|---|---|---|---|
| 0.01% | SA | 200 | 1600 | 5 | 95 | 0.08 |
| " | ECOLI | 100 | 1600 | 5 | 95 | 0.11 |
| " | PSA | 1200 | 1600 | 5 | 95 | 0.06 |
| " | PC | 1800 | 1250 | 5 | 95 | 0.08 |
| " | CAN | 100 | 15000 | 5 | 95 | 0.06 |
| " | AN | 100 | 3200 | 5 | 95 | 0.08 |
| 0.025% | SA | 200 | 1600 | 12.5 | 237.5 | 0.21 |
| " | ECOLI | 100 | 1600 | 12.5 | 237.5 | 0.27 |
| " | PSA | 1200 | 1600 | 12.5 | 237.5 | 0.16 |
| " | PC | 1800 | 1250 | 12.5 | 237.5 | 0.20 |
| " | CAN | 100 | 15000 | 12.5 | 237.5 | 0.14 |
| " | AN | 100 | 3200 | 12.5 | 237.5 | 0.20 |
| 0.05% | SA | 200 | 1600 | 25 | 475 | 0.42 |
| " | ECOLI | 100 | 1600 | 25 | 475 | 0.55 |
| " | PSA | 1200 | 1600 | 25 | 475 | 0.32 |
| " | PC | 1800 | 1250 | 25 | 475 | 0.39 |
| " | CAN | 100 | 15000 | 25 | 475 | 0.28 |
| " | AN | 100 | 3200 | 25 | 475 | 0.40 |
| 0.10% | SA | 200 | 1600 | 50 | 950 | 0.84 |
| " | ECOLI | 100 | 1600 | 50 | 950 | 1.09 |
| " | PSA | 1200 | 1600 | 50 | 950 | 0.64 |
| " | PC | 1800 | 1250 | 50 | 950 | 0.79 |
| " | CAN | 100 | 15000 | 50 | 950 | 0.56 |
| " | AN | 100 | 3200 | 50 | 950 | 0.80 |
| 0.20% | SA | 200 | 1600 | 100 | 1900 | 1.69 |
| " | ECOLI | 100 | 1600 | 100 | 1900 | 2.19 |
| " | PSA | 1200 | 1600 | 100 | 1900 | 1.27 |
| " | PC | 1800 | 1250 | 100 | 1900 | 1.58 |
| " | CAN | 100 | 15000 | 100 | 1900 | 1.13 |
| " | AN | 100 | 3200 | 100 | 1900 | 1.59 |
| 0.40% | SA | 200 | 1600 | 200 | 4800 | 4.00 |
| " | ECOLI | 100 | 1600 | 200 | 4800 | 5.00 |
| " | PSA | 1200 | 1600 | 200 | 4800 | 3.17 |
| " | PC | 1800 | 1250 | 200 | 4800 | 3.95 |
| " | CAN | 100 | 15000 | 200 | 4800 | 2.32 |
| " | AN | 100 | 3200 | 200 | 4800 | 3.50 |
| 0.50% | SA | 200 | 1600 | 250 | 4750 | 4.22 |
| " | ECOLI | 100 | 1600 | 250 | 4750 | 5.47 |
| " | PSA | 1200 | 1600 | 250 | 4750 | 3.18 |
| " | PC | 1800 | 1250 | 250 | 4750 | 3.94 |
| " | CAN | 100 | 15000 | 250 | 4750 | 2.82 |
| " | AN | 100 | 3200 | 250 | 4750 | 3.98 |

TABLE 8

2000:1 Wt. Ratio DMDMH/IPBC

| Use Level | Organism | $Q_a$ | $Q_b$ | $Q_A$ | $Q_B$ | SI |
|---|---|---|---|---|---|---|
| 0.01% | SA | 200 | 1600 | 0.05 | 99.95 | 0.06 |
| " | ECOLI | 100 | 800 | 0.05 | 99.95 | 0.13 |
| " | PSA | 1200 | 1600 | 0.05 | 99.95 | 0.06 |
| " | PC | 1800 | 1600 | 0.05 | 99.95 | 0.06 |
| " | CAN | 100 | 16000 | 0.05 | 99.95 | 0.01 |
| " | AN | 100 | 16000 | 0.05 | 99.95 | 0.01 |
| 0.025% | SA | 200 | 1600 | 0.125 | 249.88 | 0.16 |
| " | ECOLI | 100 | 800 | 0.125 | 249.88 | 0.31 |
| " | PSA | 1200 | 1600 | 0.125 | 249.88 | 0.16 |
| " | PC | 1800 | 1600 | 0.125 | 249.88 | 0.16 |
| " | CAN | 100 | 16000 | 0.125 | 249.88 | 0.02 |
| " | AN | 100 | 16000 | 0.125 | 249.88 | 0.02 |
| 0.05% | SA | 200 | 1600 | 0.25 | 499.75 | 0.31 |
| " | ECOLI | 100 | 800 | 0.25 | 499.75 | 0.63 |
| " | PSA | 1200 | 1600 | 0.25 | 499.75 | 0.31 |
| " | PC | 1800 | 1600 | 0.25 | 499.75 | 0.31 |
| " | CAN | 100 | 16000 | 0.25 | 499.75 | 0.03 |
| " | AN | 100 | 16000 | 0.25 | 499.75 | 0.03 |
| 0.10% | SA | 200 | 1600 | 0.5 | 999.5 | 0.63 |
| " | ECOLI | 100 | 800 | 0.5 | 999.5 | 1.25 |
| " | PSA | 1200 | 1600 | 0.5 | 999.5 | 0.63 |
| " | PC | 1800 | 1600 | 0.5 | 999.5 | 0.62 |
| " | CAN | 100 | 16000 | 0.5 | 999.5 | 0.07 |
| " | AN | 100 | 16000 | 0.5 | 999.5 | 0.07 |
| 0.20% | SA | 200 | 1600 | 1 | 1999 | 1.25 |
| " | ECOLI | 100 | 800 | 1 | 1999 | 2.51 |
| " | PSA | 1200 | 1600 | 1 | 1999 | 1.25 |
| " | PC | 1800 | 1600 | 1 | 1999 | 1.25 |
| " | CAN | 100 | 16000 | 1 | 1999 | 0.13 |
| " | AN | 100 | 16000 | 1 | 1999 | 0.13 |
| 0.40% | SA | 200 | 1600 | 2 | 3998 | 2.51 |
| " | ECOLI | 100 | 800 | 2 | 3998 | 5.02 |
| " | PSA | 1200 | 1600 | 2 | 3998 | 2.50 |
| " | PC | 1800 | 1600 | 2 | 3998 | 2.50 |
| " | CAN | 100 | 16000 | 2 | 3998 | 0.27 |
| " | AN | 100 | 16000 | 2 | 3998 | 0.27 |
| 0.50% | SA | 200 | 1600 | 2.5 | 4997.5 | 3.14 |
| " | ECOLI | 100 | 800 | 2.5 | 4997.5 | 6.27 |
| " | PSA | 1200 | 1600 | 2.5 | 4997.5 | 3.13 |
| " | PC | 1800 | 1600 | 2.5 | 4997.5 | 3.12 |
| " | CAN | 100 | 16000 | 2.5 | 4997.5 | 0.34 |
| " | AN | 100 | 16000 | 2.5 | 4997.5 | 0.34 |

TABLE 9

1000:1 Wt. Ratio DMDMH/IPBC

| Use Level | Organism | $Q_a$ | $Q_b$ | $Q_A$ | $Q_B$ | SI |
|---|---|---|---|---|---|---|
| 0.01.% | SA | 200 | 1600 | 0.1 | 99.9 | 0.06 |
| " | ECOLI | 100 | 800 | 0.1 | 99.9 | 0.13 |
| " | PSA | 1200 | 1600 | 0.1 | 99.9 | 0.06 |
| " | PC | 1800 | 1600 | 0.1 | 99.9 | 0.06 |
| " | CAN | 100 | 16000 | 0.1 | 99.9 | 0.01 |
| " | AN | 100 | 16000 | 0.1 | 99.9 | 0.01 |
| 0.025% | SA | 200 | 1600 | 0.25 | 249.8 | 0.16 |
| " | ECOLI | 100 | 800 | 0.25 | 249.8 | 0.31 |
| " | PSA | 1200 | 1600 | 0.25 | 249.8 | 0.16 |
| " | PC | 1800 | 1600 | 0.25 | 249.8 | 0.16 |
| " | CAN | 100 | 16000 | 0.25 | 249.8 | 0.02 |
| " | AN | 100 | 16000 | 0.25 | 249.8 | 0.02 |
| 0.05% | SA | 200 | 1600 | 0.5 | 499.5 | 0.31 |
| " | ECOLI | 100 | 800 | 0.5 | 499.5 | 0.63 |
| " | PSA | 1200 | 1600 | 0.5 | 499.5 | 0.31 |
| " | PC | 1800 | 1600 | 0.5 | 499.5 | 0.31 |
| " | CAN | 100 | 16000 | 0.5 | 499.5 | 0.04 |
| " | AN | 100 | 16000 | 0.5 | 499.5 | 0.04 |
| 0.10% | SA | 200 | 1600 | 1 | 999 | 0.63 |
| " | ECOLI | 100 | 800 | 1 | 999 | 1.26 |
| " | PSA | 1200 | 1600 | 1 | 999 | 0.63 |
| " | PC | 1800 | 1600 | 1 | 999 | 0.62 |
| " | CAN | 100 | 16000 | 1 | 999 | 0.07 |
| " | AN | 100 | 16000 | 1 | 999 | 0.07 |

TABLE 9-continued

1000:1 Wt. Ratio DMDMH/IPBC

| Use Level | Organism | $Q_a$ | $Q_b$ | $Q_A$ | $Q_B$ | SI |
|---|---|---|---|---|---|---|
| 0.20% | SA | 200 | 1600 | 2 | 1998 | 1.26 |
| " | ECOLI | 100 | 800 | 2 | 1998 | 2.52 |
| " | PSA | 1200 | 1600 | 2 | 1998 | 1.25 |
| " | PC | 1800 | 1600 | 2 | 1998 | 1.25 |
| " | CAN | 100 | 16000 | 2 | 1998 | 0.14 |
| " | AN | 100 | 16000 | 2 | 1998 | 0.14 |
| 0.40% | SA | 200 | 1600 | 4 | 3996 | 2.52 |
| " | ECOLI | 100 | 800 | 4 | 3996 | 5.04 |
| " | PSA | 1200 | 1600 | 4 | 3996 | 2.50 |
| " | PC | 1800 | 1600 | 4 | 3996 | 2.50 |
| " | CAN | 100 | 16000 | 4 | 3996 | 0.29 |
| " | AN | 100 | 16000 | 4 | 3996 | 0.29 |
| 0.50% | SA | 200 | 1600 | 5 | 4995 | 3.15 |
| " | ECOLI | 100 | 800 | 5 | 4995 | 6.29 |
| " | PSA | 1200 | 1600 | 5 | 4995 | 3.13 |
| " | PC | 1800 | 1600 | 5 | 4995 | 3.12 |
| " | CAN | 100 | 16000 | 5 | 4995 | 0.36 |
| " | AN | 100 | 16000 | 2.5 | 4997.5 | 0.36 |

TABLE 10

500:1 Wt. Ratio DMDMH/IPBC

| Use Level | Organism | $Q_a$ | $Q_b$ | $Q_A$ | $Q_B$ | SI |
|---|---|---|---|---|---|---|
| 0.01% | SA | 200 | 1600 | 0.2 | 99.8 | 0.06 |
| " | ECOLI | 100 | 800 | 0.2 | 99.8 | 0.13 |
| " | PSA | 1200 | 1600 | 0.2 | 99.8 | 0.06 |
| " | PC | 1800 | 1600 | 0.2 | 99.8 | 0.06 |
| " | CAN | 100 | 16000 | 0.2 | 99.8 | 0.01 |
| " | AN | 100 | 16000 | 0.2 | 99.8 | 0.01 |
| 0.25% | SA | 200 | 1600 | 0.5 | 249.5 | 0.16 |
| " | ECOLI | 100 | 800 | 0.5 | 249.5 | 0.32 |
| " | PSA | 1200 | 1600 | 0.5 | 249.5 | 0.16 |
| " | PC | 1800 | 1600 | 0.5 | 249.5 | 0.16 |
| " | CAN | 100 | 16000 | 0.5 | 249.5 | 0.02 |
| " | AN | 100 | 16000 | 0.5 | 249.5 | 0.02 |
| 0.05% | SA | 200 | 1600 | 1 | 499 | 0.32 |
| " | ECOLI | 100 | 800 | 1 | 499 | 0.63 |
| " | PSA | 1200 | 1600 | 1 | 499 | 0.31 |
| " | PC | 1800 | 1600 | 1 | 499 | 0.31 |
| " | CAN | 100 | 16000 | 1 | 499 | 0.04 |
| " | AN | 100 | 16000 | 1 | 499 | 0.04 |
| 0.10% | SA | 200 | 1600 | 2 | 998 | 0.63 |
| " | ECOLI | 100 | 800 | 2 | 998 | 1.27 |
| " | PSA | 1200 | 1600 | 2 | 998 | 0.63 |
| " | PC | 1800 | 1600 | 2 | 998 | 0.62 |
| " | CAN | 100 | 16000 | 2 | 998 | 0.08 |
| " | AN | 100 | 16000 | 2 | 998 | 0.08 |
| 0.20% | SA | 200 | 1600 | 4 | 1996 | 1.27 |
| " | ECOLI | 100 | 800 | 4 | 1996 | 2.54 |
| " | PSA | 1200 | 1600 | 4 | 1996 | 1.25 |
| " | PC | 1800 | 1600 | 4 | 1996 | 1.25 |
| " | CAN | 100 | 16000 | 4 | 1996 | 0.16 |
| " | AN | 100 | 16000 | 4 | 1996 | 0.16 |
| 0.40% | SA | 200 | 1600 | 8 | 3992 | 2.54 |
| " | ECOLI | 100 | 800 | 8 | 3992 | 5.07 |
| " | PSA | 1200 | 1600 | 8 | 3992 | 2.50 |
| " | PC | 1800 | 1600 | 8 | 3992 | 2.50 |
| " | CAN | 100 | 16000 | 8 | 3992 | 0.33 |
| " | AN | 100 | 16000 | 8 | 3992 | 0.33 |
| 0.50% | SA | 200 | 1600 | 10 | 4900 | 3.11 |
| " | ECOLI | 100 | 800 | 10 | 4900 | 6.23 |
| " | PSA | 1200 | 1600 | 10 | 4900 | 3.07 |
| " | PC | 1800 | 1600 | 10 | 4900 | 3.07 |
| " | CAN | 100 | 16000 | 10 | 4900 | 0.41 |
| " | AN | 100 | 16000 | 10 | 4900 | 0.41 |

TABLE 11

200:1 Wt. Ratio DMDMH/IPBC

| Use Level | Organism | $Q_a$ | $Q_b$ | $Q_A$ | $Q_B$ | SI |
|---|---|---|---|---|---|---|
| 0.01% | SA | 200 | 1600 | 0.5 | 99.5 | 0.06 |
| " | ECOLI | 100 | 800 | 0.5 | 99.5 | 0.13 |
| " | PSA | 1200 | 1600 | 0.5 | 99.5 | 0.06 |
| " | PC | 1800 | 1600 | 0.5 | 99.5 | 0.06 |
| " | CAN | 100 | 16000 | 0.5 | 99.5 | 0.01 |
| " | AN | 100 | 16000 | 0.5 | 99.5 | 0.01 |
| 0.025% | SA | 200 | 1600 | 1.25 | 248.75 | 0.16 |
| " | ECOLI | 100 | 800 | 1.25 | 248.75 | 0.32 |
| " | PSA | 1200 | 1600 | 1.25 | 248.75 | 0.16 |
| " | PC | 1800 | 1600 | 1.25 | 248.75 | 0.16 |
| " | CAN | 100 | 16000 | 1.25 | 248.75 | 0.03 |
| " | AN | 100 | 16000 | 1.25 | 248.75 | 0.03 |
| 0.05% | SA | 200 | 1600 | 2.5 | 497.5 | 0.32 |
| " | ECOLI | 100 | 800 | 2.5 | 497.5 | 0.65 |
| " | PSA | 1200 | 1600 | 2.5 | 497.5 | 0.31 |
| " | PC | 1800 | 1600 | 2.5 | 497.5 | 0.31 |
| " | CAN | 100 | 16000 | 2.5 | 497.5 | 0.06 |
| " | AN | 100 | 16000 | 2.5 | 497.5 | 0.06 |
| 0.10% | SA | 200 | 1600 | 5 | 995 | 0.65 |
| " | ECOLI | 100 | 800 | 5 | 995 | 1.29 |
| " | PSA | 1200 | 1600 | 5 | 995 | 0.63 |
| " | PC | 1800 | 1600 | 5 | 995 | 0.62 |
| " | CAN | 100 | 16000 | 5 | 995 | 0.11 |
| " | AN | 100 | 16000 | 5 | 995 | 0.11 |
| 0.20% | SA | 200 | 1600 | 10 | 1990 | 1.29 |
| " | ECOLI | 100 | 800 | 10 | 1990 | 2.59 |
| " | PSA | 1200 | 1600 | 10 | 1990 | 1.25 |
| " | PC | 1800 | 1600 | 10 | 1990 | 1.25 |
| " | CAN | 100 | 16000 | 10 | 1990 | 0.22 |
| " | AN | 100 | 16000 | 10 | 1990 | 0.22 |
| 0.40% | SA | 200 | 1600 | 20 | 3980 | 2.59 |
| " | ECOLI | 100 | 800 | 20 | 3980 | 5.18 |
| " | PSA | 1200 | 1600 | 20 | 3980 | 2.50 |
| " | PC | 1800 | 1600 | 20 | 3980 | 2.50 |
| " | CAN | 100 | 16000 | 20 | 3980 | 0.45 |
| " | AN | 100 | 16000 | 20 | 3980 | 0.45 |
| 0.50% | SA | 200 | 1600 | 25 | 4975 | 3.23 |
| " | ECOLI | 100 | 800 | 25 | 4975 | 6.47 |
| " | PSA | 1200 | 1600 | 25 | 4975 | 3.13 |
| " | PC | 1800 | 1600 | 25 | 4975 | 3.12 |
| " | CAN | 100 | 16000 | 25 | 4975 | 0.56 |
| " | AN | 100 | 16000 | 25 | 4975 | 0.56 |

TABLE 12

100:1 Wt. Ratio DMDMH/IPBC

| Use Level | Organism | $Q_a$ | $Q_b$ | $Q_A$ | $Q_B$ | SI |
|---|---|---|---|---|---|---|
| 0.01% | SA | 200 | 1600 | 1 | 99 | 0.07 |
| " | ECOLI | 100 | 800 | 1 | 99 | 0.13 |
| " | PSA | 1200 | 1600 | 1 | 99 | 0.06 |
| " | PC | 1800 | 1600 | 1 | 99 | 0.06 |
| " | CAN | 100 | 16000 | 1 | 99 | 0.02 |
| " | AN | 100 | 16000 | 1 | 99 | 0.02 |
| 0.025% | SA | 200 | 1600 | 2.5 | 248 | 0.17 |
| " | ECOLI | 100 | 800 | 2.5 | 248 | 0.33 |
| " | PSA | 1200 | 1600 | 2.5 | 248 | 0.16 |
| " | PC | 1800 | 1600 | 2.5 | 248 | 0.16 |
| " | CAN | 100 | 16000 | 2.5 | 248 | 0.04 |
| " | AN | 100 | 16000 | 2.5 | 248 | 0.04 |
| 0.05% | SA | 200 | 1600 | 5 | 495 | 0.33 |
| " | ECOLI | 100 | 800 | 5 | 495 | 0.67 |
| " | PSA | 1200 | 1600 | 5 | 495 | 0.31 |
| " | PC | 1800 | 1600 | 5 | 495 | 0.31 |
| " | CAN | 100 | 16000 | 5 | 495 | 0.08 |
| " | AN | 100 | 16000 | 5 | 495 | 0.08 |
| 0.10% | SA | 200 | 1600 | 10 | 990 | 0.67 |
| " | ECOLI | 100 | 800 | 10 | 990 | 1.34 |
| " | PSA | 1200 | 1600 | 10 | 990 | 0.63 |
| " | PC | 1800 | 1600 | 10 | 990 | 0.62 |
| " | CAN | 100 | 16000 | 10 | 990 | 0.16 |
| " | AN | 100 | 16000 | 10 | 990 | 0.16 |

TABLE 12-continued

100:1 Wt. Ratio DMDMH/IPBC

| Use Level | Organism | $Q_a$ | $Q_b$ | $Q_A$ | $Q_B$ | SI |
|---|---|---|---|---|---|---|
| 0.20% | SA | 200 | 1600 | 20 | 1980 | 1.34 |
| " | ECOLI | 100 | 800 | 20 | 1980 | 2.68 |
| " | PSA | 1200 | 1600 | 20 | 1980 | 1.25 |
| " | PC | 1800 | 1600 | 20 | 1980 | 1.25 |
| " | CAN | 100 | 16000 | 20 | 1980 | 0.32 |
| " | AN | 100 | 16000 | 20 | 1980 | 0.32 |
| 0.40% | SA | 200 | 1600 | 40 | 3960 | 2.68 |
| " | ECOLI | 100 | 800 | 40 | 3960 | 5.35 |
| " | PSA | 1200 | 1600 | 40 | 3960 | 2.51 |
| " | PC | 1800 | 1600 | 40 | 3960 | 2.50 |
| " | CAN | 100 | 16000 | 40 | 3960 | 0.65 |
| " | AN | 100 | 16000 | 40 | 3960 | 0.65 |
| 0.50% | SA | 200 | 1600 | 50 | 4950 | 3.34 |
| " | ECOLI | 100 | 800 | 50 | 4950 | 6.69 |
| " | PSA | 1200 | 1600 | 50 | 4950 | 3.14 |
| " | PC | 1800 | 1600 | 50 | 4950 | 3.12 |
| " | CAN | 100 | 16000 | 50 | 4950 | 0.81 |
| " | AN | 100 | 16000 | 50 | 4950 | 0.81 |

TABLE 13

50:1 Wt. Ratio DMDMH/IPBC

| Use Level | Organism | $Q_a$ | $Q_b$ | $Q_A$ | $Q_B$ | SI |
|---|---|---|---|---|---|---|
| 0.01% | SA | 200 | 1600 | 2 | 98 | 0.07 |
| " | ECOLI | 100 | 800 | 2 | 98 | 0.14 |
| " | PSA | 1200 | 1600 | 2 | 98 | 0.06 |
| " | PC | 1800 | 1600 | 2 | 98 | 0.06 |
| " | CAN | 100 | 16000 | 2 | 98 | 0.03 |
| " | AN | 100 | 16000 | 2 | 98 | 0.03 |
| 0.025% | SA | 200 | 1600 | 5 | 245 | 0.18 |
| " | ECOLI | 100 | 800 | 5 | 245 | 0.36 |
| " | PSA | 1200 | 1600 | 5 | 245 | 0.16 |
| " | PC | 1800 | 1600 | 5 | 245 | 0.16 |
| " | CAN | 100 | 16000 | 5 | 245 | 0.07 |
| " | AN | 100 | 16000 | 5 | 245 | 0.07 |
| 0.05% | SA | 200 | 1600 | 10 | 490 | 0.36 |
| " | ECOLI | 100 | 800 | 10 | 490 | 0.71 |
| " | PSA | 1200 | 1600 | 10 | 490 | 0.31 |
| " | PC | 1800 | 1600 | 10 | 490 | 0.31 |
| " | CAN | 100 | 16000 | 10 | 490 | 0.13 |
| " | AN | 100 | 16000 | 10 | 490 | 0.13 |
| 0.10% | SA | 200 | 1600 | 20 | 980 | 0.71 |
| " | ECOLI | 100 | 800 | 20 | 980 | 1.43 |
| " | PSA | 1200 | 1600 | 20 | 980 | 0.63 |
| " | PC | 1800 | 1600 | 20 | 980 | 0.62 |
| " | CAN | 100 | 16000 | 20 | 980 | 0.26 |
| " | AN | 100 | 16000 | 20 | 980 | 0.26 |
| 0.20% | SA | 200 | 1600 | 40 | 1960 | 1.43 |
| " | ECOLI | 100 | 800 | 40 | 1960 | 2.85 |
| " | PSA | 1200 | 1600 | 40 | 1960 | 1.26 |
| " | PC | 1800 | 1600 | 40 | 1960 | 1.25 |
| " | CAN | 100 | 16000 | 40 | 1960 | 0.52 |
| " | AN | 100 | 16000 | 40 | 1960 | 0.52 |
| 0.40% | SA | 200 | 1600 | 80 | 3920 | 2.85 |
| " | ECOLI | 100 | 800 | 80 | 3920 | 5.70 |
| " | PSA | 1200 | 1600 | 80 | 3920 | 2.52 |
| " | PC | 1800 | 1600 | 80 | 3920 | 2.49 |
| " | CAN | 100 | 16000 | 80 | 3920 | 1.05 |
| " | AN | 100 | 16000 | 80 | 3920 | 1.05 |
| 0.50% | SA | 200 | 1600 | 100 | 4900 | 3.56 |
| " | ECOLI | 100 | 800 | 100 | 4900 | 7.13 |
| " | PSA | 1200 | 1600 | 100 | 4900 | 3.15 |
| " | PC | 1800 | 1600 | 100 | 4900 | 3.12 |
| " | CAN | 100 | 16000 | 100 | 4900 | 1.31 |
| " | AN | 100 | 16000 | 100 | 4900 | 1.31 |

TABLE 14

20:1 Wt. Ratio DMDMH/IPBC

| Use Level | Organism | $Q_a$ | $Q_b$ | $Q_A$ | $Q_B$ | SI |
|---|---|---|---|---|---|---|
| 0.01% | SA | 200 | 1600 | 5 | 95 | 0.08 |
| " | ECOLI | 100 | 800 | 5 | 95 | 0.17 |
| " | PSA | 1200 | 1600 | 5 | 95 | 0.06 |
| " | PC | 1800 | 1600 | 5 | 95 | 0.06 |
| " | CAN | 100 | 16000 | 5 | 95 | 0.06 |
| " | AN | 100 | 16000 | 5 | 95 | 0.06 |
| 0.025% | SA | 200 | 1600 | 12.5 | 237.5 | 0.21 |
| " | ECOLI | 100 | 800 | 12.5 | 237.5 | 0.42 |
| " | PSA | 1200 | 1600 | 12.5 | 237.5 | 0.16 |
| " | PC | 1800 | 1600 | 12.5 | 237.5 | 0.16 |
| " | CAN | 100 | 16000 | 12.5 | 237.5 | 0.14 |
| " | AN | 100 | 16000 | 12.5 | 237.5 | 0.14 |
| 0.05% | SA | 200 | 1600 | 25 | 475 | 0.42 |
| " | ECOLI | 100 | 800 | 25 | 475 | 0.84 |
| " | PSA | 1200 | 1600 | 25 | 475 | 0.32 |
| " | PC | 1800 | 1600 | 25 | 475 | 0.31 |
| " | CAN | 100 | 16000 | 25 | 475 | 0.28 |
| " | AN | 100 | 16000 | 25 | 475 | 0.28 |
| 0.10% | SA | 200 | 1600 | 50 | 950 | 0.84 |
| " | ECOLI | 100 | 800 | 50 | 950 | 1.69 |
| " | PSA | 1200 | 1600 | 50 | 950 | 0.64 |
| " | PC | 1800 | 1600 | 50 | 950 | 0.62 |
| " | CAN | 100 | 16000 | 50 | 950 | 0.56 |
| " | AN | 100 | 16000 | 50 | 950 | 0.56 |
| 0.20% | SA | 200 | 1600 | 100 | 1900 | 1.69 |
| " | ECOLI | 100 | 800 | 100 | 1900 | 3.38 |
| " | PSA | 1200 | 1600 | 100 | 1900 | 1.27 |
| " | PC | 1800 | 1600 | 100 | 1900 | 1.24 |
| " | CAN | 100 | 16000 | 100 | 1900 | 1.12 |
| " | AN | 100 | 16000 | 100 | 1900 | 1.12 |
| 0.40% | SA | 200 | 1600 | 200 | 4800 | 4.00 |
| " | ECOLI | 100 | 800 | 200 | 4800 | 8.00 |
| " | PSA | 1200 | 1600 | 200 | 4800 | 3.17 |
| " | PC | 1800 | 1600 | 200 | 4800 | 3.11 |
| " | CAN | 100 | 16000 | 200 | 4800 | 2.30 |
| " | AN | 100 | 16000 | 200 | 4800 | 2.30 |
| 0.50% | SA | 200 | 1600 | 250 | 4750 | 4.22 |
| " | ECOLI | 100 | 800 | 250 | 4750 | 8.44 |
| " | PSA | 1200 | 1600 | 250 | 4750 | 3.18 |
| " | PC | 1800 | 1600 | 250 | 4750 | 3.11 |
| " | CAN | 100 | 16000 | 250 | 4750 | 2.80 |
| " | AN | 100 | 16000 | 250 | 4750 | 2.80 |

Similar SI results also were found with GADM and SUTTOCIDE® A as the methylol compound in place of Germall® II or DMDMH in admixtures with IPBC over the same wt. ratios and use level ranges as shown in the Tables 1–14 above.

Tables 1 through 14 above illustrate the synergism of IPBC (compound B) with Germall® II or DMDMH (compound A) at weight ratios of A:B of 2000:1, 1000:1, 500:1, 200:1, 100:1, 50:1 and 20:1. Synergism is very effective for all ratios at low use levels, e.g. 0.01% to 0.1%, against all tested gram-positive, gram-negative organisms and fungi organisms. At slightly higher use concentrations, e.g. 0.20 to 0.50%, all tested ratios were synergistic against Candida albicans and A. niger also. However, at 50:1 and 20:1 ratios, the synergistic effect is negligible at the 0.01 to 0.1% use levels, and non-synergistic even against Candida albicans and A. niger at use levels of 0.20 to 0.50%.

The SI values were lower for Germall® II as the methylol compound in the admixtures as compared to DMDMH.

Similar results were obtained when iodopropynyl alcohol (IPGA) was substituted for IPBC in the admixtures described above.

3. PRESERVATIVE ACTIVITY (CHALLENGE TEST)

A typical cosmetic emulsion was prepared for microbiological challenge testing and predetermined admixtures of a methylol compound and IPBC were added at various use levels. The emulsion thus prepared had the following composition:

|  | % wt. |
|---|---|
| Phase A | |
| Stearic Acid | 5.00 |
| Mineral Oil | 2.50 |
| Cetyl Alcohol | 1.00 |
| Lareth-5 and Ceteth-5 and Oleth-5 and Steareth-5 | 0.50 |
| Glycerol Monostearate and Polyoxyethylene Stearate | 1.50 |
| Phase B | |
| Deionized Water | 88.0 |
| Triethanolamine 99% | 1.00 |
| Citric Acid 30% aqueous solution | 0.60 |
| Preservative Admixture | qs |

To prepare the emulsion, Phases A and B were heated separately to 75°–80° C. Phase A then was added to Phase B with mixing. The mixture then was cooled to 55°–60° C. At this point the desired amount of the preservative admixture was added and the product was cooled to 50° C. while stirring. The citric acid solution then was added to adjust the pH and the mixture was stirred until a temperature of 30° C. was reached.

The challenge tests were carried out using the following microorganisms: SA, ECOLI, PSA, PC, AN and CAN, in this manner. 50 g. aliquots of the test emulsion containing various amounts of the preservative admixture were inoculated with approximately 10⁷–10⁸ of the challenge organisms. The test samples then were stirred to disperse the challenge inoculum. The samples were incubated and assayed at 48 hours, 7, 14, 21 and 28 days. The assays were performed on 1 g. of the test sample by serially diluting $10^1$ to $10^6$ of the original concentration. The plating medium for bacteria was Letheen agar and for fungi it was low pH Mycophil agar with Tween 20. Each plated sample was incubated for 48 hours at 37° C. for bacteria, 5 days at 25° C. for mold, and 3 days at 25° C. for fungi. After incubation, readings of the number of colonies per milliliter (cfu/ml) were made. At 21 days the test product was reinoculated with half of the original inoculum. The data is presented in Tables 15–23 below.

TABLE 15

2000:1 GERMALL ® II/IPBC

| Test Level | Organism | 48 Hours | 7 Days | 14 Days | 21 Days | 28 Days |
|---|---|---|---|---|---|---|
| 0.01% | AN | 69,000 | 260,000 | 190,000 | 17,000 | 4,500 |
| " | CAN | 98,000 | 76,000 | 1,400 | 3,100 | 19,000 |
| " | ECOLI | 110,000 | 290,000 | 2,400 | 138,000 | 560,000 |
| " | PC | <10 | <10 | <10 | <10 | <10 |
| " | PSA | <10 | <10 | <10 | <10 | <10 |
| " | SA | 190,000 | 220 | <10 | <10 | 3,700 |
| 0.025% | AN | 2,800 | 10 | 10 | <10 | 220 |
| " | CAN | 58,000 | 29,000 | 18,000 | 56,000 | 110,000 |
| " | ECOLI | 39,000 | 10 | <10 | <10 | <10 |
| " | PC | <10 | <10 | <10 | <10 | <10 |
| " | PSA | <10 | <10 | <10 | <10 | <10 |

TABLE 15-continued

2000:1 GERMALL ® II/IPBC

| Test Level | Organism | 48 Hours | 7 Days | 14 Days | 21 Days | 28 Days |
|---|---|---|---|---|---|---|
| " | SA | 37,000 | 170 | <10 | <10 | <10 |
| 0.05% | AN | 20 | <10 | <10 | <10 | <10 |
| " | CAN | 19,000 | 6,600 | 70 | <10 | 320 |
| " | ECOLI | 3,400 | <10 | <10 | <10 | <10 |
| " | PC | <10 | <10 | <10 | <10 | <10 |
| " | PSA | <10 | <10 | <10 | <10 | <10 |
| " | SA | 31,000 | <10 | <10 | <10 | <10 |
| 0.1% | AN | <10 | <10 | <10 | <10 | <10 |
| " | CAN | 180 | <10 | <10 | <10 | <10 |
| " | ECOLI | <10 | <10 | <10 | <10 | <10 |
| " | PC | <10 | <10 | <10 | <10 | <10 |
| " | PSA | <10 | <10 | <10 | <10 | <10 |
| " | SA | 750 | <10 | <10 | <10 | <10 |
| 0.2% | AN | <10 | <10 | <10 | <10 | <10 |
| " | CAN | <10 | <10 | <10 | <10 | <10 |
| " | ECOLI | <10 | <10 | <10 | <10 | <10 |
| " | PC | <10 | <10 | <10 | <10 | <10 |
| " | PSA | <10 | <10 | <10 | <10 | <10 |
| " | SA | <10 | <10 | <10 | <10 | <10 |

Unpreserved control

| Organism | 48 Hours | 7 Days | 14 Days | 21 Days | 28 Days |
|---|---|---|---|---|---|
| AN | 52,000 | 27,000 | 19,000 | 19,000 | 19,000 |
| CAN | 110,000 | 130,000 | 240,000 | 180,000 | 240,000 |
| ECOLI | 54,000 | 140,000 | 170,000 | 170,000 | 74,000 |
| PC | 6,400,000 | 6,400,000 | 2,000,000 | 6,700,000 | 29,000 |
| PSA | 110,000 | 700 | 110,000 | 290,000 | 85,000 |
| SA | 2,800,000 | 250,000 | 51,000 | 3,700 | 330 |

Inoculum Concentration

| Organism | 0 Hours | 21 Days |
|---|---|---|
| AN | 26,000 | 53,000 |
| CAN | 1,000,000 | 1,900,000 |
| ECOLI | 3,600,000 | 170,000 |
| PC | 3,400,000 | 87,000 |
| PSA | 4,500,000 | 390,000 |
| SA | 4,100,000 | 200,000 |

TABLE 16

1000:1 GERMALL ® II/IPBC

| Test Level | Organism | 48 Hours | 7 Days | 14 Days | 21 Days | 28 Days |
|---|---|---|---|---|---|---|
| 0.01% | AN | 34,000 | 3,500 | 80 | 10 | <10 |
| " | CAN | 420,000 | 24,000 | 950 | 6,400 | 6,400,000 |
| " | ECOLI | 120,000 | 63,000 | 93,000 | 92,000 | 9,600,000 |
| " | PC | 10 | 25,000 | 1,600 | 15,800 | 33,000,000 |
| " | PSA | <10 | <10 | <10 | <10 | <10 |
| " | SA | 100,000 | 1,400 | <10 | <10 | 5,000 |
| 0.025% | AN | 530 | 10 | <10 | <10 | <10 |
| " | CAN | 34,000 | 750 | 10 | 770 | 240,000 |
| " | ECOLI | 120,000 | <10 | <10 | <10 | <10 |
| " | PC | <10 | <10 | <10 | <10 | <10 |
| " | PSA | <10 | <10 | <10 | <10 | <10 |
| " | SA | 37,000 | 170 | <10 | <10 | <10 |
| 0.05% | AN | <10 | <10 | <10 | <10 | <10 |
| " | CAN | 13,000 | <10 | <10 | <10 | <10 |
| " | ECOLI | 68,000 | <10 | <10 | <10 | <10 |
| " | PC | <10 | <10 | <10 | <10 | <10 |
| " | PSA | <10 | <10 | <10 | <10 | <10 |
| " | SA | 21,000 | <10 | <10 | <10 | <10 |
| 0.1% | AN | <10 | <10 | <10 | <10 | <10 |
| " | CAN | 10 | <10 | <10 | <10 | <10 |
| " | ECOLI | <10 | <10 | <10 | <10 | <10 |
| " | PC | <10 | <10 | <10 | <10 | <10 |
| " | PSA | <10 | <10 | <10 | <10 | <10 |
| " | SA | 1,400 | <10 | <10 | <10 | <10 |
| 0.2% | AN | <10 | <10 | <10 | <10 | <10 |
| " | CAN | <10 | <10 | <10 | <10 | <10 |

TABLE 16-continued

1000:1 GERMALL ® II/IPBC

| | | | | | | |
|---|---|---|---|---|---|---|
| " | ECOLI | <10 | <10 | <10 | <10 | <10 |
| " | PC | <10 | <10 | <10 | <10 | <10 |
| " | PSA | <10 | <10 | <10 | <10 | <10 |
| " | SA | <10 | <10 | <10 | <10 | <10 |

Unpreserved control

| Organism | 48 Hours | 7 Days | 14 Days | 21 Days | 28 Days |
|---|---|---|---|---|---|
| AN | 52,000 | 27,000 | 19,000 | 19,000 | 19,000 |
| CAN | 110,000 | 130,000 | 240,000 | 180,000 | 240,000 |
| ECOLI | 54,000 | 140,000 | 170,000 | 170,000 | 74,000 |
| PC | 6,400,000 | 6,400,000 | 2,000,000 | 6,700,000 | 29,000 |
| PSA | 110,000 | 700 | 110,000 | 290,000 | 85,000 |

TABLE 16-continued

1000:1 GERMALL ® II/IPBC

| | | | | | |
|---|---|---|---|---|---|
| SA | 2,800,000 | 250,000 | 51,000 | 3,700 | 330 |

Inoculum Concentration

| Organism | 0 Hours | 21 Days |
|---|---|---|
| AN | 26,000 | 53,000 |
| CAN | 1,000,000 | 1,900,000 |
| ECOLI | 3,600,000 | 170,000 |
| PC | 3,400,000 | 87,000 |
| PSA | 4,500,000 | 390,000 |
| SA | 4,100,000 | 200,000 |

TABLE 17

500:1 GERMALL ® II/IPBC

| Test Level | Organism | 48 Hours | 7 Days | 14 Days | 21 Days | 28 Days |
|---|---|---|---|---|---|---|
| 0.01% | AN | 23,000 | 40 | <10 | <10 | <10 |
| " | CAN | 170,000 | 5,600 | 290 | 200 | <10 |
| " | ECOLI | 90,000 | 57,000 | 95,000 | 70,000 | 240,000 |
| " | PC | 10 | <10 | <10 | >10,000 | 42,000,000 |
| " | PSA | <10 | <10 | <10 | <10 | <10 |
| " | SA | 380,000 | 440 | <10 | <10 | 5,100 |
| 0.05% | AN | <10 | <10 | <10 | <10 | <10 |
| " | CAN | 8,700 | <10 | <10 | <10 | <10 |
| " | ECOLI | 60,000 | <10 | <10 | <10 | <10 |
| " | PC | <10 | <10 | <10 | <10 | <10 |
| " | PSA | <10 | <10 | <10 | <10 | <10 |
| " | SA | 31,000 | <10 | <10 | <10 | <10 |
| 0.1% | AN | <10 | <10 | <10 | <10 | <10 |
| " | CAN | <10 | <10 | <10 | <10 | <10 |
| " | ECOLI | <10 | <10 | <10 | <10 | <10 |
| " | PC | <10 | <10 | <10 | <10 | <10 |
| " | PSA | <10 | <10 | <10 | <10 | <10 |
| " | SA | 890 | <10 | <10 | <10 | <10 |
| 0.2% | AN | <10 | <10 | <10 | <10 | <10 |
| " | CAN | <10 | <10 | <10 | <10 | <10 |
| " | ECOLI | <10 | <10 | <10 | <10 | <10 |
| " | PC | <10 | <10 | <10 | <10 | <10 |
| " | PSA | <10 | <10 | <10 | <10 | <10 |
| " | SA | <10 | <10 | <10 | <10 | <10 |

Unpreserved control

| Organism | 48 Hours | 7 Days | 14 Days | 21 Days | 28 Days |
|---|---|---|---|---|---|
| AN | 6,100 | 520,000 | 18,000 | 5,000 | 11,000 |
| CAN | 1,000,000 | 710,000 | 95,000 | 12,000 | 64,000 |
| ECOLI | 7,100,000 | 6,200,000 | 610,000 | 350,000 | 120,000 |
| PC | 14,600,000 | 160,000,000 | 3,600,000 | 2,720,000 | 9,500,000 |
| PSA | 20 | 900 | 130 | 4,100 | >100,000 |
| SA | 43,000,000 | 600,000 | 1,000 | 220 | <10 |

Inoculum Concentration

| Organism | 0 Hours | 21 Days |
|---|---|---|
| AN | 19,000 | 4,700,000 |
| CAN | 340,000 | 16,000,000 |
| ECOLI | 3,900,000 | 1,480,000 |
| PC | 3,800,000 | 1,380,000 |
| PSA | 9,200,000 | 730,000 |
| SA | 4,800,000 | 360,000 |

TABLE 18

200:1 GERMALL® II/IPBC

| Test Level | Organism | 48 Hours | 7 Days | 14 Days | 21 Days | 28 Days |
|---|---|---|---|---|---|---|
| 0.01% | AN | 47,000 | 320 | 10 | <10 | <10 |
| " | CAN | 810,000 | 450,000 | 410,000 | 190,000 | 63,000 |
| " | ECOLI | 220,000 | 7,600 | <10 | 850 | >1,000,000 |
| " | PC | 10,000 | 500,000 | 1,900,000 | 1,100,000 | 193,000 |
| " | PSA | <10 | <10 | <10 | <10 | <10 |
| " | SA | 190,000 | 23,000 | 120 | <10 | <10 |
| 0.05% | AN | <10 | <10 | <10 | <10 | <10 |
| " | CAN | 190 | <10 | <10 | <10 | <10 |
| " | ECOLI | 37,000 | <10 | <10 | <10 | <10 |
| " | PC | <10 | <10 | <10 | <10 | <10 |
| " | PSA | <10 | <10 | <10 | <10 | <10 |
| " | SA | 19,000 | <10 | <10 | <10 | <10 |
| 0.1% | AN | <10 | <10 | <10 | <10 | <10 |
| " | CAN | 10 | <10 | <10 | <10 | <10 |
| " | ECOLI | <10 | <10 | <10 | <10 | <10 |
| " | PC | <10 | <10 | <10 | <10 | <10 |
| " | PSA | <10 | <10 | <10 | <10 | <10 |
| " | SA | 45,000 | <10 | <10 | <10 | <10 |
| 0.2% | AN | <10 | <10 | <10 | <10 | <10 |
| " | CAN | <10 | <10 | <10 | <10 | <10 |
| " | ECOLI | <10 | <10 | <10 | <10 | <10 |
| " | PC | <10 | <10 | <10 | <10 | <10 |
| " | PSA | <10 | <10 | <10 | <10 | <10 |
| " | SA | <10 | <10 | <10 | <10 | <10 |

Unpreserved control

| Organism | 48 Hours | 7 Days | 14 Days | 21 Days | 28 Days |
|---|---|---|---|---|---|
| AN | 89,000 | 32,000 | 22,000 | 16,000 | 16,000 |
| CAN | 210,000 | 670,000 | 430,000 | 590,000 | 640,000 |
| ECOLI | 640,000 | 360,000 | 410,000 | 990,000 | 68,000 |
| PC | 19,000,000 | 3,200,000 | 7,000,000 | >10,000 | 2,760,000 |
| PSA | 80 | 9,400 | 200,000 | >10,000 | 34,000 |
| SA | 6,300,000 | 190,000 | 11,000 | 580 | 120 |

Inoculum Concentration

| Organism | 0 Hours | 21 Days |
|---|---|---|
| AN | 41,000 | 32,000 |
| CAN | 640 | 1,100,000 |
| ECOLI | 5,800,000 | 1,300,000 |
| PC | 900,000 | 3,000,000 |
| PSA | 1,800,000 | 4,900,000 |
| SA | 7,200,000 | 2,000,000 |

TABLE 19

50:1 GERMAL® II/IPBC

| Test Level | Organism | 48 Hours | 7 Days | 14 Days | 21 Days | 28 Days |
|---|---|---|---|---|---|---|
| 0.01% | AN | 4,100 | 40 | <10 | <10 | <10 |
| " | CAN | 310,000 | 7,700 | 560 | 5,600 | 5,200 |
| " | ECOLI | 170,000 | 710 | 10 | <10 | 120 |
| " | PC | 7,400 | 74,000 | 340,000 | 720,000 | 520,000 |
| " | PSA | <10 | <10 | <10 | <10 | 30 |
| " | SA | 110,000 | 11,000 | <10 | <10 | 9,200 |
| 0.05% | AN | <10 | 100 | <10 | <10 | <10 |
| " | CAN | 210 | <10 | <10 | <10 | <10 |
| " | ECOLI | 150,000 | <10 | <10 | <10 | <10 |
| " | PC | <10 | <10 | <10 | <10 | <10 |
| " | PSA | <10 | <10 | <10 | <10 | <10 |
| " | SA | 35,000 | <10 | <10 | <10 | <10 |
| 0.1% | AN | <10 | <10 | <10 | <10 | <10 |
| " | CAN | <10 | <10 | <10 | <10 | <10 |
| " | ECOLI | 510 | <10 | <10 | <10 | <10 |
| " | PC | <10 | <10 | <10 | <10 | <10 |
| " | PSA | <10 | <10 | <10 | <10 | <10 |
| " | SA | 3,000 | <10 | <10 | <10 | <10 |
| 0.2% | AN | <10 | <10 | <10 | <10 | <10 |
| " | CAN | <10 | <10 | <10 | <10 | <10 |
| " | ECOLI | <10 | <10 | <10 | <10 | <10 |
| " | PC | <10 | <10 | <10 | <10 | <10 |
| " | PSA | <10 | <10 | <10 | <10 | <10 |
| " | SA | <10 | <10 | <10 | <10 | <10 |

Unpreserved control

| Organism | 48 Hours | 7 Days | 14 Days | 21 Days | 28 Days |
|---|---|---|---|---|---|
| AN | 89,000 | 32,000 | 22,000 | 16,000 | 16,000 |
| CAN | 210,000 | 670,000 | 430,000 | 590,000 | 640,000 |
| ECOLI | 640,000 | 360,000 | 410,000 | 990,000 | 68,000 |
| PC | 19,000,000 | 3,200,000 | 7,000,000 | >10,000 | 2,760,000 |
| PSA | 80 | 9,400 | 200,000 | >10,000 | 34,000 |
| SA | 6,300,000 | 190,000 | 11,000 | 580 | 120 |

TABLE 19-continued

50:1 GERMAL ® II/IPBC

| | Inoculum Concentration | |
|---|---|---|
| Organism | 0 Hours | 21 Days |
| AN | 41,000 | 32,000 |
| CAN | 640 | 1,100,000 |
| ECOLI | 5,800,000 | 1,300,000 |
| PC | 900,000 | 3,000,000 |
| PSA | 1,800,000 | 4,900,000 |
| SA | 7,200,000 | 2,000,000 |

TABLE 20

20:1 GERMALL ® II/IPBC

| Test Level | Organism | 48 Hours | 7 Days | 14 Days | 21 Days | 28 Days |
|---|---|---|---|---|---|---|
| 0.01% | AN | 3,100 | <10 | <10 | <10 | <10 |
| " | CAN | 75,000 | 220 | <10 | <10 | 2,400 |
| " | ECOLI | 160,000 | 110 | <10 | <10 | 20 |
| " | PC | 12,000 | 1,000,000 | 2,100,000 | >1,000,000 | 730,000 |
| " | PSA | <10 | <10 | <10 | <10 | 4,000 |
| " | SA | 140,000 | 4,100 | <10 | <10 | 1,680 |
| 0.05% | AN | <10 | <10 | <10 | <10 | <10 |
| " | CAN | <10 | <10 | <10 | <10 | <10 |
| " | ECOLI | 16,000 | <10 | <10 | <10 | <10 |
| " | PC | <10 | <10 | <10 | <10 | <10 |
| " | PSA | <10 | <10 | | <10 | <10 |
| " | SA | 31,000 | <10 | <10 | <10 | <10 |
| 0.1% | AN | <10 | <10 | <10 | <10 | <10 |
| " | CAN | <10 | <10 | <10 | <10 | <10 |
| " | ECOLI | <10 | <10 | <10 | <10 | <10 |
| " | PC | <10 | <10 | <10 | <10 | <10 |
| " | PSA | <10 | <10 | <10 | <10 | <10 |
| " | SA | 6,800 | <10 | <10 | <10 | <10 |
| 0.2% | AN | <10 | <10 | <10 | <10 | <10 |
| " | CAN | <10 | <10 | <10 | <10 | <10 |
| " | ECOLI | <10 | <10 | <10 | <10 | <10 |
| " | PC | <10 | <10 | <10 | <10 | <10 |
| " | PSA | <10 | <10 | <10 | <10 | <10 |
| " | SA | <10 | <10 | <10 | <10 | <10 |

| | Unpreserved control | | | | |
|---|---|---|---|---|---|
| Organism | 48 Hours | 7 Days | 14 Days | 21 Days | 28 Days |
| AN | 89,000 | 32,000 | 22,000 | 16,000 | 16,000 |
| CAN | 210,000 | 670,000 | 430,000 | 590,000 | 640,000 |
| ECOLI | 640,000 | 360,000 | 410,000 | 990,000 | 68,000 |
| PC | 19,000,000 | 3,200,000 | 7,000,000 | >10,000 | 2,760,000 |
| PSA | 80 | 9,400 | 200,000 | >10,000 | 34,000 |
| SA | 6,300,000 | 190,000 | 11,000 | 580 | 120 |

| | Inoculum Concentration | |
|---|---|---|
| Organism | 0 Hours | 21 Days |
| AN | 41,000 | 32,000 |
| CAN | 640 | 1,100,000 |
| ECOLI | 5,800,000 | 1,300,000 |
| PC | 900,000 | 3,000,000 |
| PSA | 1,800,000 | 4,900,000 |
| SA | 7,200,000 | 2,000,000 |

TABLE 21

2000:1 DMDMH/IPBC

| Test Level | Organism | 48 Hours | 7 Days | 14 Days | 21 Days | 28 Days |
|---|---|---|---|---|---|---|
| 0.025% | AN | 4,100 | 38,000 | 270 | 80 | 100 |
| " | CAN | 270,000 | 1,900,000 | 550,000 | 220,000 | 210,000 |
| " | ECOLI | 1,300,000 | <10 | <10 | <10 | 3,000 |
| " | PC | <10 | <10 | <10 | <10 | <10 |
| " | PSA | <10 | <10 | <10 | <10 | <10 |
| " | SA | 42,000 | 20 | <10 | <10 | <10 |
| 0.05% | AN | <10 | <10 | <10 | <10 | <10 |

TABLE 21-continued

2000:1 DMDMH/IPBC

| | Organism | 48 Hours | 7 Days | 14 Days | 21 Days | 28 Days |
|---|---|---|---|---|---|---|
| " | CAN | 770,000 | 130,000 | 670,000 | 160,000 | 64,000 |
| " | ECOLI | 220,000 | <10 | <10 | <10 | <10 |
| " | PC | <10 | <10 | <10 | <10 | <10 |
| " | PSA | <10 | <10 | <10 | <10 | <10 |
| " | SA | 9,000 | <10 | <10 | <10 | <10 |
| 0.1% | AN | <10 | <10 | <10 | <10 | <10 |
| " | CAN | 580 | 840 | 500 | 40,000 | 83,000 |
| " | ECOLI | 340 | <10 | <10 | <10 | <10 |
| " | PC | <10 | <10 | <10 | <10 | <10 |
| " | PSA | <10 | <10 | <10 | <10 | <10 |
| " | SA | 29,000 | <10 | <10 | <10 | <10 |
| 0.2% | AN | <10 | <10 | <10 | <10 | <10 |
| " | CAN | <10 | 10 | 10 | <10 | 21 |
| " | ECOLI | <10 | <10 | <10 | <10 | <10. |
| " | PC | <10 | <10 | <10 | <10 | <10 |
| " | PSA | <10 | <10 | <10 | <10 | <10 |
| " | SA | <10 | <10 | <10 | <10 | <10 |

Unpreserved control

| Organism | 48 Hours | 7 Days | 14 Days | 21 Days | 28 Days |
|---|---|---|---|---|---|
| AN | 37,000 | 36,000 | 24,000 | 5,200 | 6,000 |
| CAN | 120,000 | 1,900,000 | 3,300,000 | 480,000 | 790,000 |
| ECOLI | 150,000 | 2,500,000 | 7,300,000 | 240,000 | 140,000 |
| PC | 19,000,000 | 15,600,000 | 5,900,000 | 8,500,000 | 31,000,000 |
| PSA | <10 | <10 | 100 | 15,200 | 300,000 |
| SA | 7,000,000 | >1,000,000 | 12,000 | 3,000 | 110 |

Inoculum Concentration

| Organism | 0 Hours | 21 Days |
|---|---|---|
| AN | 50,000 | 41,000 |
| CAN | 1,400,000 | 640 |
| ECOLI | 4,800,000 | 5,800,000 |
| PC | 9,200,000 | 900,000 |
| PSA | 6,900,000 | 9,000,000 |
| SA | 5,700,000 | 7,200,000 |

TABLE 22

1000:1 DMDMH/IPBC

| Test Level | Organism | 48 Hours | 7 Days | 14 Days | 21 Days | 28 Days |
|---|---|---|---|---|---|---|
| 0.025% | AN | 650 | 900 | <10 | <10 | 140 |
| " | CAN | 97,000 | 900,000 | 2,300,000 | 120,000 | 120,000 |
| " | ECOLI | 160,000 | <10 | <10 | <10 | 2,400 |
| " | PC | <10 | <10 | <10 | <10 | <10 |
| " | PSA | <10 | <10 | <10 | <10 | <10 |
| " | SA | 23,000 | <10 | <10 | <10 | 90 |
| 0.05% | AN | 20 | <10 | <10 | <10 | <10 |
| " | CAN | 65,000 | 520,000 | 56,000 | 32,000 | 370,000 |
| " | ECOLI | 26,000 | <10 | <10 | <10 | <10 |
| " | PC | <10 | <10 | <10 | <10 | <10 |
| " | PSA | <10 | <10 | <10 | <10 | <10 |
| " | SA | 12,000 | <10 | <10 | <10 | <10 |
| 0.1% | AN | <10 | <10 | <10 | <10 | <10 |
| " | CAN | 3,100 | 4,800 | 180 | 640 | 4,400 |
| " | ECOLI | 45,000 | <10 | <10 | <10 | <10 |
| " | PC | <10 | <10 | <10 | <10 | <10 |
| " | PSA | <10 | <10 | <10 | <10 | <10 |
| " | SA | 6,000 | <10 | <10 | <10 | <10 |
| 0.2% | AN | <10 | <10 | <10 | <10 | <10 |
| " | CAN | <10 | <10 | <10 | <10 | <10 |
| " | ECOLI | <10 | <10 | <10 | <10 | <10 |
| " | PC | <10 | <10 | <10 | <10 | <10 |
| " | PSA | <10 | <10 | <10 | <10 | <10 |
| " | SA | 180 | <10 | <10 | <10 | <10 |

TABLE 22-continued

1000:1 DMDMH/IPBC

Unpreserved control

| Organism | 48 Hours | 7 Days | 14 Days | 21 Days | 28 Days |
|---|---|---|---|---|---|
| AN | 37,000 | 36,000 | 24,000 | 5,200 | 6,000 |
| CAN | 120,000 | 1,900,000 | 3,300,000 | 480,000 | 790,000 |
| ECOLI | 150,000 | 2,500,000 | 7,300,000 | 240,000 | 140,000 |
| PC | 19,000,000 | 15,600,000 | 5,900,000 | 8,500,000 | 31,000,000 |
| PSA | <10 | <10 | 100 | 15,200 | 300,000 |
| SA | 7,000,000 | >1,000,000 | 12,000 | 3,000 | 110 |

Inoculum Concentration

| Organism | 0 Hours | 21 Days |
|---|---|---|
| AN | 50,000 | 41,000 |
| CAN | 1,400,000 | 640 |
| ECOLI | 4,800,000 | 5,800,000 |
| PC | 9,200,000 | 900,000 |
| PSA | 6,900,000 | 9,000,000 |
| SA | 5,700,000 | 7,200,000 |

TABLE 23

2000:1 GADM/IPBC

| Test Level | Organism | 48 Hours | 7 Days | 14 Days | 21 Days | 28 Days |
|---|---|---|---|---|---|---|
| 0.025% | AN | 300 | 21 | 10 | <10 | 11 |
| " | CAN | 480,000 | 890,000 | 940,000 | 1,040,000 | 130,000 |
| " | ECOLI | 230,000 | <10 | <10 | <10 | <10 |
| " | PC | <10 | <10 | <10 | <10 | <10 |
| " | PSA | <10 | <10 | <10 | <10 | <10 |
| " | SA | 78,000 | <10 | <10 | <10 | <10 |
| 0.05% | AN | <10 | <10 | <10 | <10 | <10 |
| " | CAN | 110,000 | 4,100,000 | 3,600,000 | 330,000 | 97,000 |
| " | ECOLI | 120,000 | <10 | <10 | <10 | <10 |
| " | PC | <10 | <10 | <10 | <10 | <10 |
| " | PSA | <10 | <10 | <10 | <10 | <10 |
| " | SA | 56,000 | <10 | <10 | <10 | <10 |
| 0.1% | AN | <10 | <10 | <10 | <10 | <10 |
| " | CAN | 1,200,000 | 53,000 | 430,000 | 144,000 | 110,000 |
| " | ECOLI | <10 | <10 | <10 | <10 | <10 |
| " | PC | <10 | <10 | <10 | <10 | <10 |
| " | PSA | <10 | <10 | <10 | <10 | <10 |
| " | SA | <10 | <10 | <10 | <10 | <10 |
| 0.2% | AN | <10 | <10 | <10 | <10 | <10 |
| " | CAN | 90,000 | <10 | <10 | <10 | 60 |
| " | ECOLI | <10 | <10 | <10 | <10 | <10 |
| " | PC | <10 | <10 | <10 | <10 | <10 |
| " | PSA | <10 | <10 | <10 | <10 | <10 |
| " | SA | <10 | <10 | <10 | <10 | <10 |

Unpreserved control

| Organism | 48 Hours | 7 Days | 14 Days | 21 Days | 28 Days |
|---|---|---|---|---|---|
| AN | 50,000 | 33,000 | 33,000 | 13,000 | 5,400 |
| CAN | 780,000 | 780,000 | 780,000 | 500,000 | 170,000 |
| ECOLI | 600,000 | 3,100,000 | 920,000 | 920,000 | 140,000 |
| PC | 11,000,000 | 30,000,000 | 10,000,000 | 10,000,000 | 1,400,000 |
| PSA | 3,800 | 600 | 12,800 | 12,800 | 100,000 |
| SA | 14,000,000 | 410,000 | 7,100 | 7,100 | 80 |

Inoculum Concentration

| Organism | 0 Hours | 21 Days |
|---|---|---|
| AN | 53,000 | 10,000 |
| CAN | 1,900,000 | 310,000 |
| ECOLI | 170,000 | 3,500,000 |
| PC | 87,000 | 2,500,000 |
| PSA | 390,000 | 5,400,000 |
| SA | 200,000 | 4,100,000 |

Discussion of Challenge Testing Results

The 28-day challenge results reported in Tables 15–23 above demonstrate the effectiveness of the preservative admixture of the invention in a use emulsion composition against a wide range of bacteria and fungi organisms.

For example, admixture compositions of Germall® II and IPBC at a wt. ratio of 2000:1 (Table 15), when present at use levels of 0.05 to 0.2%, corresponding to 0.75 to 10 ppm IPBC and 500 to 2000 ppm methylol levels, provide substantially complete protection against all tested organisms after 28 days. At the low use level of 0.05% active, all the challenge tests passed within 21 days. Then, upon reinoculation after 21 days, all organisms died within 7 days except CAN which cleared within 14 days.

Table 21 shows the challenge test results for DMDMH and IPBC admixtures at the same 2000:1 wt. ratio. A use level of 0.2%, however, is needed for this blend to pass against all organisms after 21 days. Upon reinoculation, all organisms died within 7 days with the exception of CAN which cleared within 14 days. It is thus evident from these results that Germall® II blended with IPBC is 4 times more effective than a DMDMH/IPBC blend.

Germall® II also is superior to GADM as the methylol compound, as shown in Table 23.

While the invention has been described with particular reference to certain embodiments thereof, it will be understood that changes and modifications may be made which are within the skill of the art. Accordingly, it is intended to be bound only by the following claims, in which:

What is claimed is:

1. A water soluble preservative antimicrobial composition for addition to commercial use products at predetermined use levels to provide synergistic biocidal activity against a wide range of fungi and gram-negative and gram-positive bacteria, comprising an admixture of
   (a) 1,3-dimethylol-5,5-dimethyl hydantoin, and
   (b) 3-iodo-2-propynylbutyl carbamate, in a weight ratio of (a):(b) of 100:1 to 2000:1.

2. A water soluble preservative admixture according to claim 1 wherein said weight ratio is 200:1 to 500:1.

3. A preservative admixture according to claim 1 wherein
   (a) also includes N-[1,3-bis(hydroxymethyl)-2,5-dioxo-4-imidazolidinyl]-N,N'-bis(hydroxymethyl) urea.

4. A commercial use product which is protected for an extended period of time against contamination by a wide range of fungi and gram-negative and gram-positive bacteria which includes 0.01 to 0.5% by weight of the water soluble preservative concentrate of claim 1.

5. A commercial use product according to claim 4 which includes about 0.1% by weight of the water soluble preservative concentrate of claim 2.

6. A commercial use product according to claim 4 in which said concentrate is water solubilized and uniformly distributed throughout said composition.

7. A commercial use product according to claim 4 in which (b) is present therein in an amount of 0.5 to 10 ppm, and (a) is present in an amount of at least 250 ppm.

8. A commercial use product according to claim 4 which is a personal care, household or industrial composition.

* * * * *